(12) United States Patent
McClurg et al.

(10) Patent No.: US 8,920,440 B2
(45) Date of Patent: Dec. 30, 2014

(54) SUTURE ASSEMBLY AND SYSTEM

(75) Inventors: Steven McClurg, Roseville, MN (US); Christopher Anthony Thierfelder, Minneapolis, MN (US); Allen Gaynor, Coon Rapids, MN (US); Timothy Andrew Bachman, St. Paul, MN (US); Christian Richard Trifilio, St. Paul, MN (US); Matthew Vail Leyden, St. Paul, MN (US)

(73) Assignee: Coloplast A/S, Humlebaek (DE)

( * ) Notice: Subject to any disclaimer, the term of this patent is extended or adjusted under 35 U.S.C. 154(b) by 0 days.

(21) Appl. No.: 12/850,644

(22) Filed: Aug. 5, 2010

(65) Prior Publication Data

US 2011/0046645 A1    Feb. 24, 2011

Related U.S. Application Data

(63) Continuation of application No. 12/813,517, filed on Jun. 11, 2010.

(30) Foreign Application Priority Data

Aug. 21, 2009  (DK) ............................. PA 2009 70093
Jun. 21, 2010  (DK) ............................. PA 2010 70278

(51) Int. Cl.
*A61B 17/04*    (2006.01)
*A61B 17/06*    (2006.01)
(52) U.S. Cl.
CPC ....... *A61B 17/06123* (2013.01); *A61B 17/0469* (2013.01); *A61B 17/06133* (2013.01); *A61B 17/06004* (2013.01); *A61B 2017/0479* (2013.01)
USPC .......................................... 606/145; 606/144

(58) Field of Classification Search
USPC ........................................ 606/139, 144–146
See application file for complete search history.

(56) References Cited

U.S. PATENT DOCUMENTS 2,029,975 A   2/1936  Winchester
2,376,151 A   5/1945  Karle
2,376,152 A   5/1945  Karle (Continued)

FOREIGN PATENT DOCUMENTS

DE    3223153 C1   8/1983
FR    1238904      7/1960

(Continued)

OTHER PUBLICATIONS

Technical examination report in the corresponding DK application No. PA 2010 70277, dated Sep. 29, 2010.

(Continued)

*Primary Examiner* — Gregory Anderson
(74) *Attorney, Agent, or Firm* — Coloplast Corp., Coloplast A/S; Nick Baumann

(57) ABSTRACT

A suture assembly configured to load a suture instrument with suture includes a cap attached to an end of the suture, a suture container configured to retain a portion of the suture, and a cap retainer having a wall and a suture channel formed in the wall. The suture channel is configured to receive a length of the suture, and the wall is configured to deny passage of the cap into the suture channel and align the cap with the length of the suture for loading into the suture instrument.

11 Claims, 16 Drawing Sheets

(56) References Cited

U.S. PATENT DOCUMENTS

| | | | |
|---|---|---|---|
| 2,824,709 A | 2/1958 | Macy | |
| 3,112,825 A | 12/1963 | Hammond et al. | |
| 3,376,973 A | 4/1968 | Granowitz et al. | |
| 3,545,608 A * | 12/1970 | Schneider | 206/63.3 |
| 3,638,653 A | 2/1972 | Berry | |
| 3,802,438 A | 4/1974 | Wolvek | |
| 4,440,171 A | 4/1984 | Nomoto et al. | |
| 4,699,271 A | 10/1987 | Lincoln et al. | |
| 4,706,843 A | 11/1987 | Thornton | |
| 5,123,911 A * | 6/1992 | Granger et al. | 606/224 |
| 5,131,534 A * | 7/1992 | Brown et al. | 206/63.3 |
| 5,192,483 A | 3/1993 | Kilgrow et al. | |
| 5,201,743 A * | 4/1993 | Haber et al. | 606/147 |
| 5,263,585 A | 11/1993 | Lawhon et al. | |
| 5,271,495 A | 12/1993 | Alpern | |
| 5,290,300 A | 3/1994 | Cosgrove et al. | |
| 5,306,281 A | 4/1994 | Beurrier | |
| 5,307,924 A | 5/1994 | Manosalva et al. | |
| 5,364,407 A | 11/1994 | Poll | |
| 5,392,903 A | 2/1995 | Sinn | |
| 5,472,081 A | 12/1995 | Kilgrow et al. | |
| 5,478,344 A | 12/1995 | Stone et al. | |
| 5,478,345 A | 12/1995 | Stone et al. | |
| 5,496,336 A | 3/1996 | Cosgrove et al. | |
| 5,562,683 A | 10/1996 | Chan | |
| 5,568,865 A | 10/1996 | Mase et al. | |
| 5,630,825 A | 5/1997 | de la Torre et al. | |
| 5,683,402 A | 11/1997 | Cosgrove et al. | |
| 5,704,469 A | 1/1998 | Daniele et al. | |
| 5,755,729 A | 5/1998 | de la Torre et al. | |
| 5,792,153 A | 8/1998 | Swain et al. | |
| 5,918,733 A | 7/1999 | Cerwin et al. | |
| 5,931,844 A | 8/1999 | Thompson et al. | |
| 5,992,787 A | 11/1999 | Burke | |
| 6,283,993 B1 | 9/2001 | Cosgrove et al. | |
| 6,551,330 B1 | 4/2003 | Bain et al. | |
| 6,802,860 B2 | 10/2004 | Cosgrove et al. | |
| 7,090,690 B2 | 8/2006 | Foerster et al. | |
| 7,407,505 B2 * | 8/2008 | Sauer et al. | 606/145 |
| 7,445,626 B2 | 11/2008 | Songer et al. | |
| 8,075,573 B2 | 12/2011 | Gambale et al. | |
| 8,226,666 B2 | 7/2012 | Zarbatany et al. | |
| 8,257,368 B2 | 9/2012 | McIntosh | |
| 2002/0143234 A1 | 10/2002 | LoVuolo | |
| 2003/0122023 A1 | 7/2003 | Pitcher | |
| 2003/0149447 A1 | 8/2003 | Morency et al. | |
| 2003/0204195 A1 | 10/2003 | Keane et al. | |
| 2004/0068273 A1 * | 4/2004 | Fariss et al. | 606/144 |
| 2004/0097968 A1 | 5/2004 | Shikhman et al. | |
| 2004/0111114 A1 | 6/2004 | Shikhman et al. | |
| 2004/0186340 A1 | 9/2004 | Reed et al. | |
| 2005/0033319 A1 | 2/2005 | Gambale et al. | |
| 2005/0143762 A1 | 6/2005 | Paraschac et al. | |
| 2006/0047289 A1 | 3/2006 | Fogel | |
| 2006/0069397 A1 | 3/2006 | Nobles et al. | |
| 2006/0184200 A1 | 8/2006 | Jervis | |
| 2007/0255296 A1 | 11/2007 | Sauer | |
| 2008/0045976 A1 | 2/2008 | Gibbons, Jr. et al. | |
| 2008/0051833 A1 | 2/2008 | Gramuglia et al. | |
| 2009/0005793 A1 | 1/2009 | Pantages et al. | |
| 2009/0069824 A1 | 3/2009 | Chu | |
| 2010/0084294 A1 | 4/2010 | Kirsch et al. | |
| 2010/0130990 A1 | 5/2010 | Saliman | |
| 2010/0331623 A1 | 12/2010 | Sauer et al. | |
| 2011/0022063 A1 | 1/2011 | McClurg et al. | |
| 2011/0118758 A1 | 5/2011 | Sauer | |
| 2011/0130773 A1 | 6/2011 | Saliman et al. | |
| 2011/0196387 A1 | 8/2011 | Pantages et al. | |
| 2011/0224698 A1 | 9/2011 | Deitch | |
| 2011/0270280 A1 | 11/2011 | Saliman | |
| 2012/0221022 A1 | 8/2012 | Devens, Jr. et al. | |
| 2012/0316582 A1 | 12/2012 | Nobles et al. | |
| 2012/0323263 A1 | 12/2012 | McClurg et al. | |

FOREIGN PATENT DOCUMENTS

| | | |
|---|---|---|
| FR | 2320253 | 3/1977 |
| GB | 2368575 | 5/2002 |
| WO | 9922648 | 5/1999 |
| WO | 2009005527 | 1/2009 |

OTHER PUBLICATIONS

Technical examination report in the corresponding DK application No. PA 2010 70278, dated Oct. 1, 2010.
EPO Partial Search Report in related application No. PCT/DK2010/050214, dated Mar. 28, 2011.
Notice of Allowance mailed on Aug. 28, 2013 in U.S. Appl. No. 13/414,738.
Office Action mailed on Aug. 26, 2013 in U.S. Appl. No. 12/850,642.
Office Action mailed on Feb. 6, 2014 in U.S. Appl. No. 13/187,522.
Office Action mailed on Jan. 6, 2012 in U.S. Appl. No. 12/813,517.
Office Action mailed on Apr. 25, 3013 in U.S. Appl. No. 13/414,738.
Office Action mailed on Apr. 23, 2014 in U.S. Appl. No. 12/813,517.

* cited by examiner

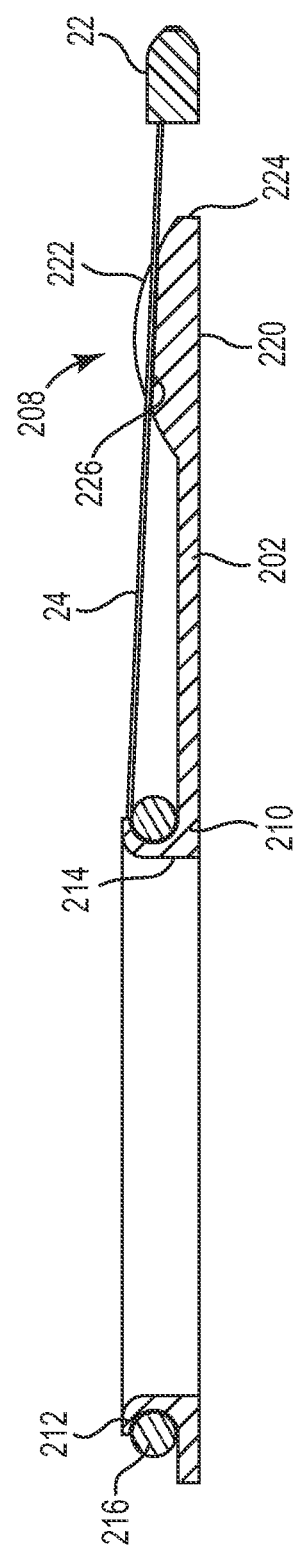

US 8,920,440 B2

SUTURE ASSEMBLY AND SYSTEM

BACKGROUND

Intracorporeal suturing of tissue during surgery presents challenges to the surgeon in that the surgeon is called upon to manipulate suturing instruments within the confines of a relatively small incision formed in the patient's body. In some cases, the surgeon is unable to see the suture site and will digitally palpate within the incision to locate a landmark for the desired placement of the suture. In any regard, once the suture placement site is identified, the surgeon will deliver at least one, but typically multiple, sutures to the site.

Improved devices and methods for loading suture instruments with suture would be welcomed by the surgical staff

SUMMARY

One aspect provides a suture assembly configured to load a suture instrument with suture. The suture assembly includes a cap attached to an end of the suture, a suture container configured to retain a portion of the suture, and a cap retainer having a wall and a suture channel formed in the wall. The suture channel is configured to receive a length of the suture, and the wall is configured to deny passage of the cap into the suture channel and align the cap with the length of the suture for loading into the suture instrument.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 15 is a cross-sectional view of the suture assembly illustrated in FIG. 14 according to one embodiment.

DETAILED DESCRIPTION

Figure 1:
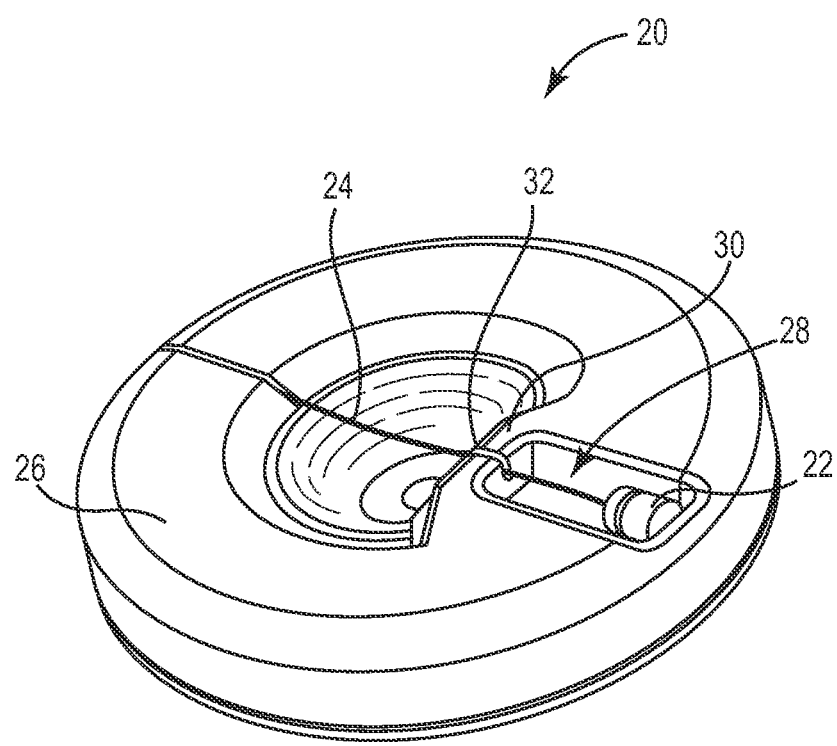
FIG. 1 is a perspective view of a suture assembly configured to organize suture according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft, tissue, which includes dermal tissue, sub-dermal tissue, ligaments, tendons, or membranes. As employed in this specification, the term "tissue" does not include bone.

In this specification, end means endmost and end portion means that segment that is adjacent to and extends from the end. For example, a proximal end is that end location of a handheld instrument that is nearest a user, and a proximal end portion is that segment (e.g., a handle of the handheld instrument) that is adjacent to and extends distally away from the proximal end.

Embodiments of the suture system and assembly described herein are useful in suturing tissue in a variety of surgical procedures, including the intracorporeal placement of sutures in the treatment of pelvic organ prolapse. The suture systems and assemblies described herein enable the rapid and convenient loading, of a suture instrument with suture. In addition, after the suture is introduced to the instrument, the suture systems and assemblies described herein provide for a tensioning mechanism to offer the surgeon improved control of the suture, even when accessing small intracorporeal incisions.

The suture systems and assemblies may be suitably employed in a wide range of suture placement applications, including suturing a scaffold or other support structure to a ligament or other tissue to support the urethra or the pelvic floor and the pelvic organs. For example, in some surgical procedures it is desirable to access a small incision in the patient and apply sutures to the sacrospinous ligament and/or in the arcus tendineus ligament or other tissue to attach a synthetic scaffold thereto that is configured to support the pelvic floor and minimize or eliminate the undesirable effects of pelvic organ prolapse.

One aspect provides a suture assembly configured to load a suture instrument with suture. The suture assembly includes a suture container configured to retain a portion of the suture, and a cap retainer configured to retain a cap (or capsule) that is attached to one end of the suture. The cap retainer includes a wall and a suture channel formed in the wall. The suture is aligned in the suture channel and the wall is configured to deny passage of the cap into the suture channel. In this manner, the cap retainer is configured to align the cap with a length of suture for loading the suture into the surgical instrument.

In one embodiment, the suture assembly is provided as a component that is removably attached to a card. The suture assembly is delivered on the card, which provides increased surface area to enable the healthcare worker to conveniently handle/manipulate the suture assembly.

One aspect provides a suture system that includes a suture instrument and a suture assembly attachable to the suture instrument. The suture instrument includes a handle that is located proximal and ahead that is located distal relative to the instrument. The head includes a distal end that defines a cavity. The suture assembly includes a cap attached to an end of the suture, a suture container maintaining a trailing section of the suture, and a cap retainer. The cap retainer is configured to isolate the capsule in a stored position away from the trailing section of the suture. When the capsule is captured in the cavity of the distal end of the head and the suture container is attached to the handle, the suture is optionally tensioned between the head and the handle of a surgical instrument.

FIG. 1 is a perspective view of one embodiment of a suture assembly 20 configured to load a suture instrument with suture. The suture assembly 20 includes a capsule 22 attached to an end of a suture 24, a suture container 26 configured to retain a portion of suture 24, and a cap retainer 28. Cap retainer 28 includes a wall 30 and a suture channel 32 formed in wall 30. The suture channel 32 is configured to receive a length of suture 24, and wall 30 is configured to deny passage of capsule 22 into suture channel 32. In this manner, the suture container 26 stores suture 24 and cap retainer 28 aligns capsule 22 with suture 24 for subsequent extraction by a suture instrument.

Figure 2:
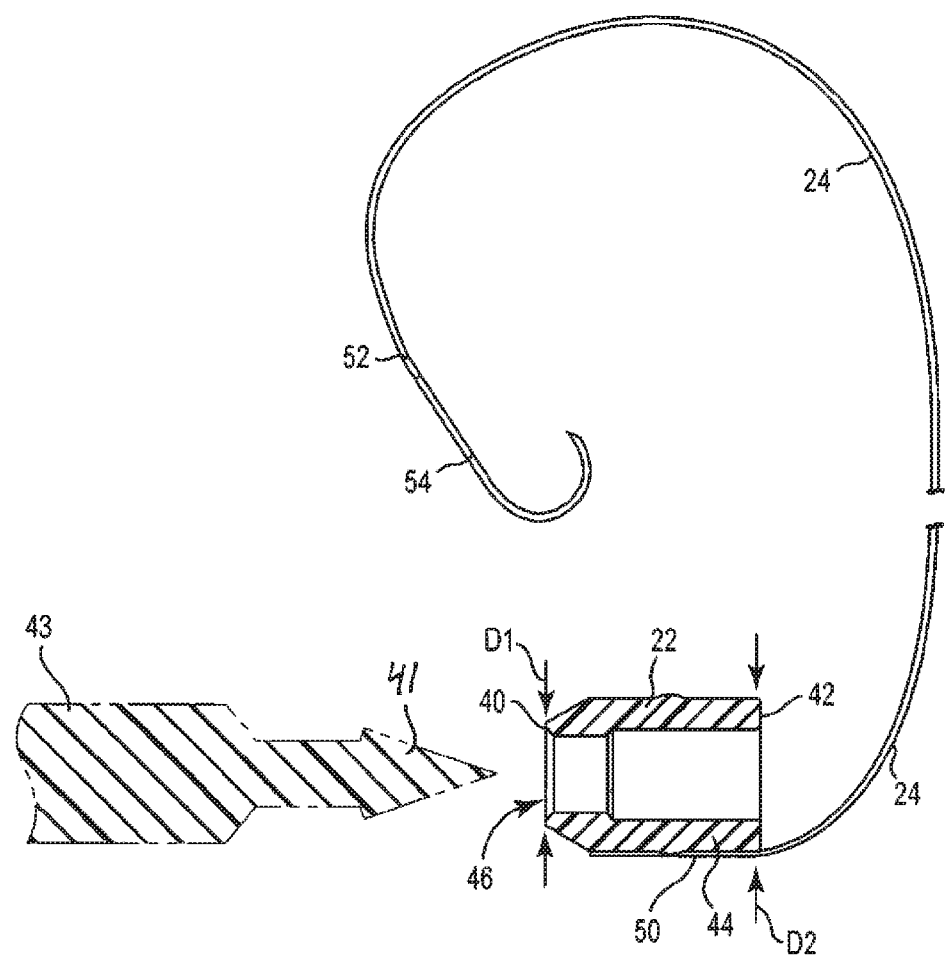
FIG. 2 is a side view of one embodiment of suture including a cap in cross-section attached to one end a suture needle attached to an opposite end.

FIG. 2 is a cross-sectional side view of capsule 22 attached to suture 24. In one embodiment, capsule 22 includes a body 44 extending between a leading end 40 having a diameter D1 and a trailing end 42 having diameter D2. In one embodiment, leading end 40 defines a recess 46 that is sized to receive a tissue-piercing pointed end 41 of a needle 43 from the suture instrument. During use, needle 43 from the suture instrument is thrown distally to allow the pointed end 41 to form an incision in the tissue; the needle 43 travels further distally to subsequently engage the pointed end 41 of the needle 43 with capsule 22 by insertion into recess 46. The needle 43 thereafter pulls the leading end 40 of capsule 22 through the tissue ahead of the trailing end 42. In one embodiment, capsule 22 is configured such that diameter D1 is smaller than diameter D2, which provides leading end 40 with the pointed end 41 that facilitates movement of leading end 40 through the tissue. In one embodiment, diameter D1 is substantially the same as diameter D2.

In one embodiment, suture 24 includes a leading end 50 attached to capsule 22 and a trailing end 52 attached to a suturing needle 54. In one embodiment, leading end 50 of suture 24 is attached to body 44 of capsule 22, although other locations for attachment of suture 24 to capsule 22 are within the scope of this disclosure. Any suitable means for attaching suture 24 to capsule 22 is acceptable, including mechanical attachments or chemical bonds. However, in one embodiment both capsule 22 and suture 24 are provided as similar materials, for example polypropylene, and leading end 50 of suture 24 is molded integrally into body 44 of capsule 22.

Suturing needle 54 is employed to selectively place a support mesh within the patient. For example, as regards the treatment of pelvic organ prolapse, the surgeon creates an incision in the patient, palpates tissue inside the incision for a location of the placement of suture 24, and employs a suitably configured instrument to throw capsule 22 through the tissue landmark. The surgeon gathers leading end 50 and trailing end 52 of suture 24 at a location exterior the incision. Thereafter, suturing needle 54 is threaded into the support mesh, and the support mesh is subsequently delivered along suture 24 to the tissue landmark and thus placed in its supportive location, in one embodiment, capsule 22 on leading end 50 is crossed-over needle 54 on an opposing end of suture 24 to form a pulley knot, and the ends of suture 24 are pulled such that the pulley knot delivers the support mesh to the tissue landmark in a pulley-fashion. Another "stay" knot is placed in suture 24 and suturing needle 54 and capsule 22 are eventually removed to terminate suture 24 on the support mesh.

In one embodiment, capsule 22 is molded from polypropylene or other polymer having a melting point similar to suture 24, which enables suture 24 to be thermally "welded" to capsule 22. Suitable suture materials include suture employed by surgeons in the treatment of pelvic organ prolapse, such as polypropylene suture, or the suture identified as Deklene, Deknatel brand suture, as available from Teleflex Medical, Mansfield, Mass., or suture available from Ethicon, Johnson&Johnson Company, located in Somerville, N.J.

Figure 3:
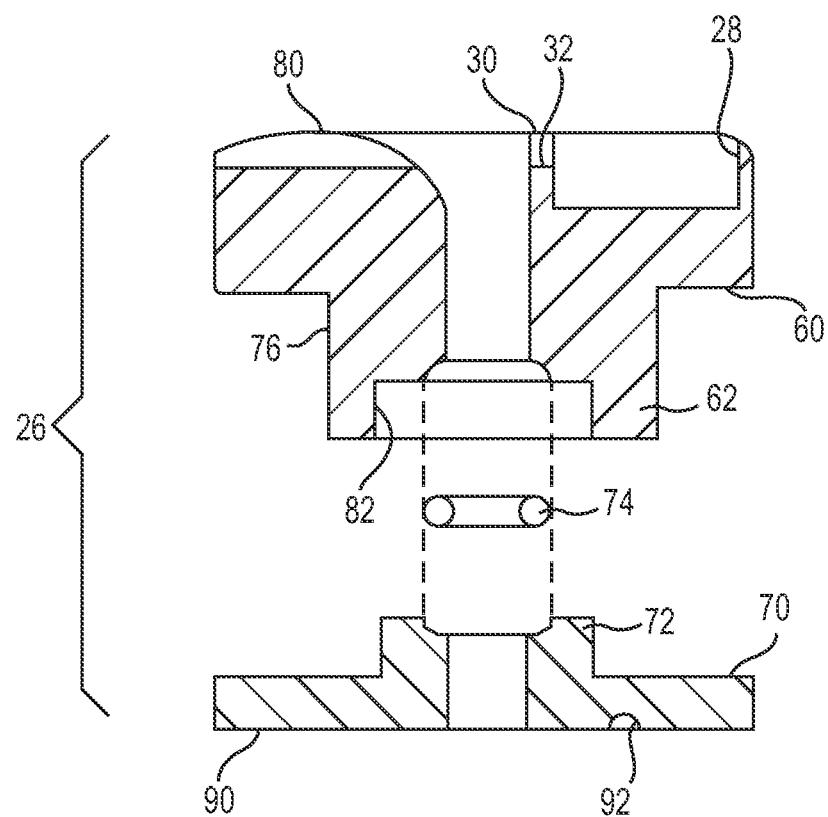
FIG. 3 is an exploded cross-sectional view of the suture assembly illustrated in FIG. 1 according to one embodiment.
Figure 4A:
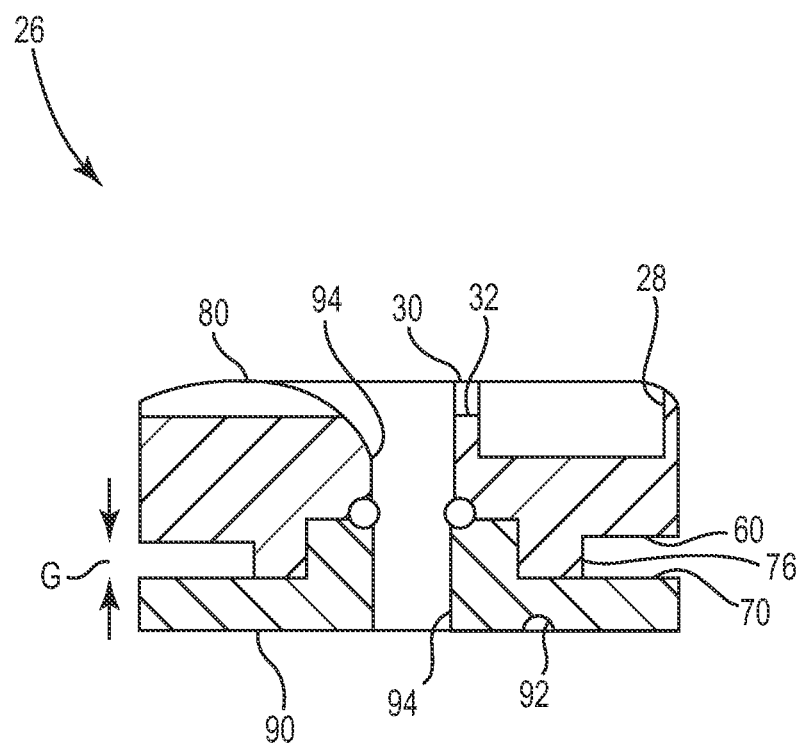
FIG. 4A is a cross-sectional view of the suture assembly illustrated in FIG. 1.
Figure 5:
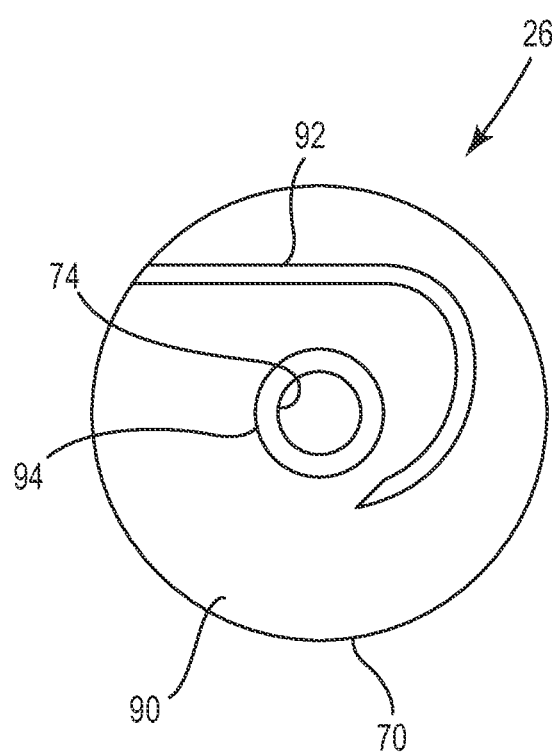
FIG. 5 is a bottom view of the suture assembly illustrated in FIG. 1.

FIG. 3 is an exploded cross-sectional view, FIG. 4A is an assembled cross-sectional view, and FIG. 5 is a bottom view of one embodiment of suture container 26 having an integrally formed capsule retainer 28.

Referring to FIGS. 3 and 4A, in one embodiment suture container 26 includes a first flange 60 extending from a first reel segment 62, a second flange 70 extending from a second reel segment 72, where the reel segments 62, 72 mate to form a suture winding surface 76, and an O-ring 74 captured between the two mated reel segments 62, 72.

In one embodiment, capsule retainer 28 is integrally formed as a recess in an exterior surface 80 of first flange 60. Suture container 26 is adapted to be fabricated as a unitary or monolithically molded device, however, in one embodiment first reel segment 62 defines an annular ring 82 that is sized to snap over second reel segment 72 to capture O-ring 74 between first reel segment 62 and second reel segment 72.

When assembled, first reel segment 62 is attached to second reel segment 72 such that first flange 60 is spaced apart from second flange 70 by a suture gap G. In one embodiment, suture gap G is selected to be substantially equal to or slightly less than a diameter of suture 24. In this manner, when suture 24 is wound onto suture winding surface 76, suture 24 is friction-fit into gap G and successive windings of suture 24 are organized in a first-in, last-out arrangement that minimizes tangling of suture 24 as it is removed from container 26.

With additional reference to FIGS. 1 and 2, in one embodiment a second flange 70 includes an exterior surface 90 that defines a needle groove 92 (FIG. 5) sized to receive suturing needle 54. Suture container 26 is configured to stow suturing needle 54 within needle groove 92 of flange 70 and capsule 22 within capsule retainer 28 of flange 60 along with a desired length of suture 24 that is wound onto suture winding surface 76. In the stowed state, capsule 22 is deposited/secured in capsule retainer 28 and a portion of suture 24 that is adjacent to leading end 50 of suture 24 is aligned in suture channel 32 formed in wall 30. In this manner, wall 30 denies passage of capsule 22 into suture channel 32 and aligns capsule 22 with the aligned length of suture 24, which orients capsule 22 and suture 24 for loading into the suture instrument.

Suitable materials for fabricating suture container 26 include plastics, including thermoplastics such as polyolefin, clear polycarbonate, or thermosets such as epoxy or reinforced epoxy. In one embodiment, suture container 26 is molded from polypropylene as a two-piece assembly including first flange 60 and second flange 70, where the two components are subsequently mated, welded, or otherwise attached over O-ring 74.

With reference to FIGS. 4A and 5, each flange 60, 70 defines a center hole 94, and O-ring 74 is captured between flanges 60, 70 such that a portion of O-ring 74 is exposed within center hole 94. In one embodiment, O-ring 74 is formed of a resilient flexible material (e.g., rubber) such that the portion of O-ring 74 that is exposed within center hole 94 will stretch when pressed onto a spindle or other post-like structure.

In one embodiment, suture assembly 26 provides a suture container that is configured to be loaded onto, or cooperate with, any of a variety of suture instruments, where assembly 26 provides suture having a bullet-shaped needle or a capsule attached to an end of the suture. Suture container 26 thus includes first flange 60 communicating with second flange 70 via a suture winding surface 76 onto which the suture is wound, and at least one of the first and second flanges 60, 70 define a recess 28 configured to retain the capsule or bullet-shaped needle.

Figure 4B:
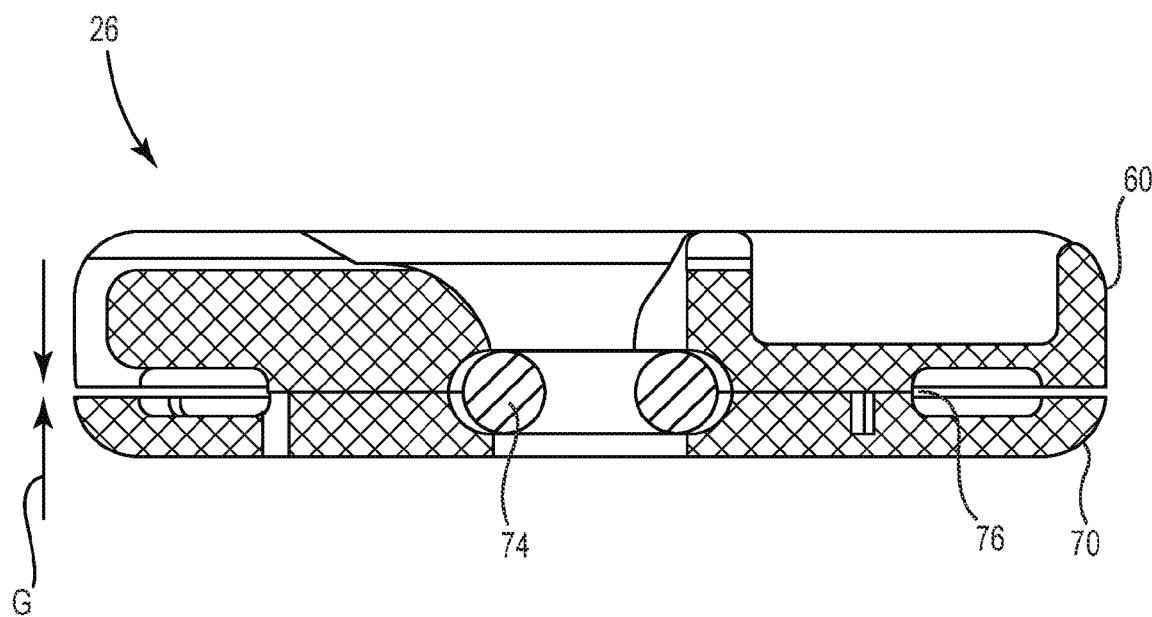
FIG. 4B is a cross-sectional view of another embodiment of the suture assembly illustrated in FIG. 1.

FIG. 4B is a cross-sectional view of another embodiment of the suture assembly 26 illustrated in FIG. 1. In this embodiment, suture container 26 includes first flange 60 attached to second flange 70 to form the suture winding surface 76 that is centered on a part line of flanges 60, 70, where O-ring 74 is captured within an annular recess formed in the two flanges 60, 70. In one embodiment, attachment posts (not visible in this view) are formed on a mating surface of flange 70 and are configured to be friction fit into a set of complementary post holes formed in a mating surface of flange 60 to facilitate assembling container 26.

In one embodiment, the first flange 60 component, the second flange 70 component, and the suture winding surface 76 are formed as a single monolithic unit, for example as a suture reel as illustrated at 26. In an exemplary embodiment, suture container 26 is molded from plastic as a monolithic reel and provided to suture suppliers or suture instrument suppliers. The suppliers load suture container 26 with their preferred or desired suture, which is wound onto surface 76. One end of the suture includes a bullet-shaped needle or a capsule attached to the suture, where the bullet-shaped needle or capsule is stored within capsule retainer 28 until loaded into the suture instrument. As an example, in one embodiment the bullet-shaped needle cooperates with a needle driver of the suture instrument that drives the bullet-shaped needle through tissue when "throwing a suture." The end of the suture opposite the bullet-shaped needle or the capsule may be provided as a free end, or a suturing needle may be attached to this end to enable closing of the surgical incision formed to receive the intracorporeal suture instrument.

Figure 6:
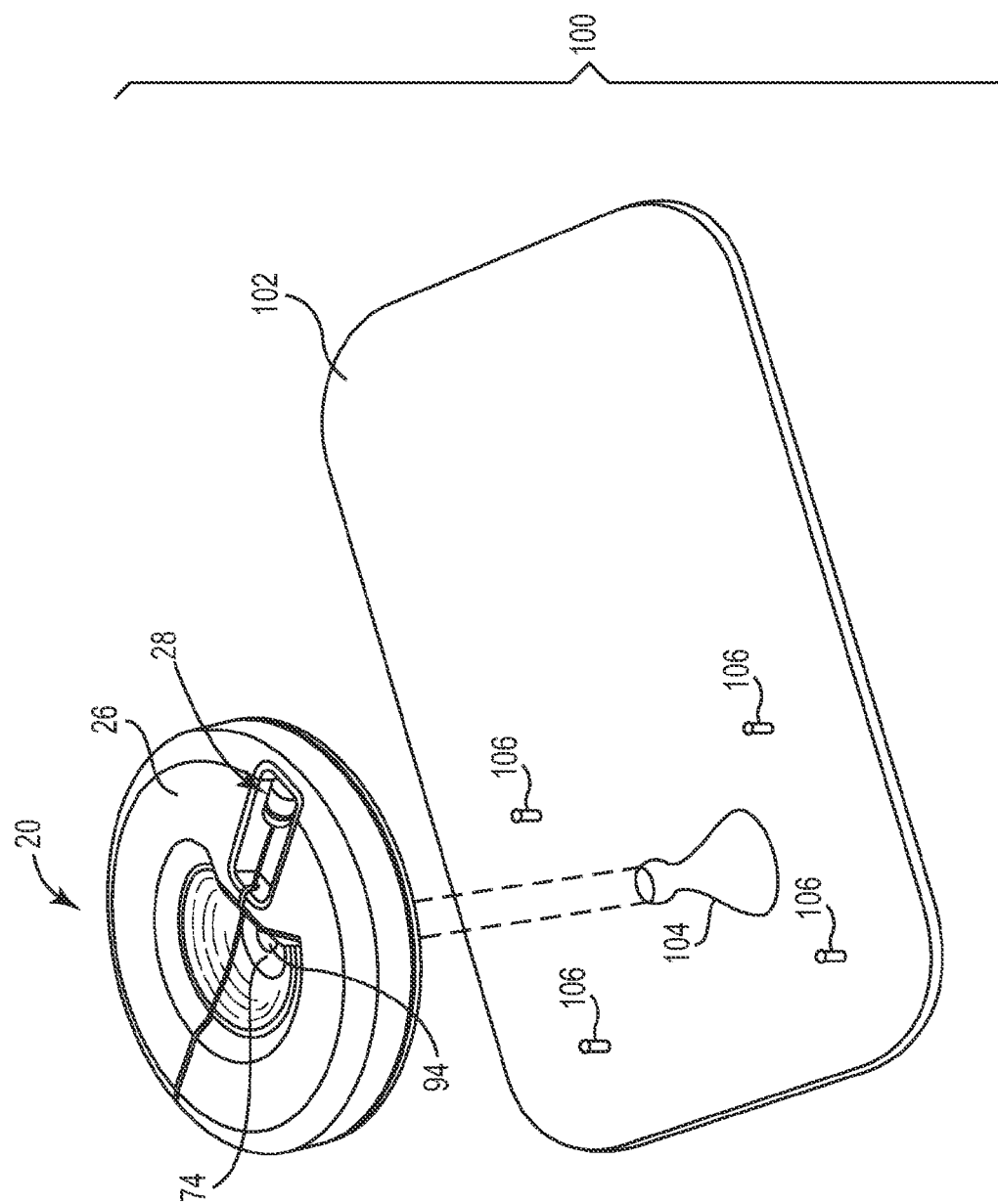
FIG. 6 is a perspective view of the suture assembly illustrated in FIG. 1 aligned for attachment to a base substrate according to one embodiment.

FIG. 6 is a perspective view of another embodiment of a suture assembly 100 including a base substrate 102 configured to hold and deliver suture assembly 20. It can be desirable to provide suture container 26 in a format that is convenient for handling when wearing surgical gloves. To facilitate the ease of handling, one embodiment of base substrate 102 provides a suture card that includes a post 104 and support feet 106. O-ring 74 of suture assembly 20 is sized to be press-fit onto post 104. Support feet 106 prevent suture container 26 from wobbling on post 104 and provide clearance between suture assembly 20 and base substrate 102, which offers leverage that is useful in separating the two components.

Base substrate 102 is preferably formed of a plastic (i.e., polypropylene) or other suitable disposable material and is sized to be approximately twice as long as the diameter of suture container 26, which provides an area on one side of base substrate 102 for grasping assembly 100. Other suitable materials and sizes for substrate 102 are also acceptable.

In one embodiment, post 104 is integrally formed to extend from substrate 102 and is provided as a cone-shape or hourglass-shape. Post 104 is sized to be pressed into hole 94 and frictionally coupled with O-ring 74. During use, suture container 26 is removed from post 104 of suture card 102 and placed on a surgical stand (e.g., a Mayo stand) for access by the surgeon when needed. The suture card 102 is disposed in a suitable waste stream determined by the surgical facility.

Figure 7:
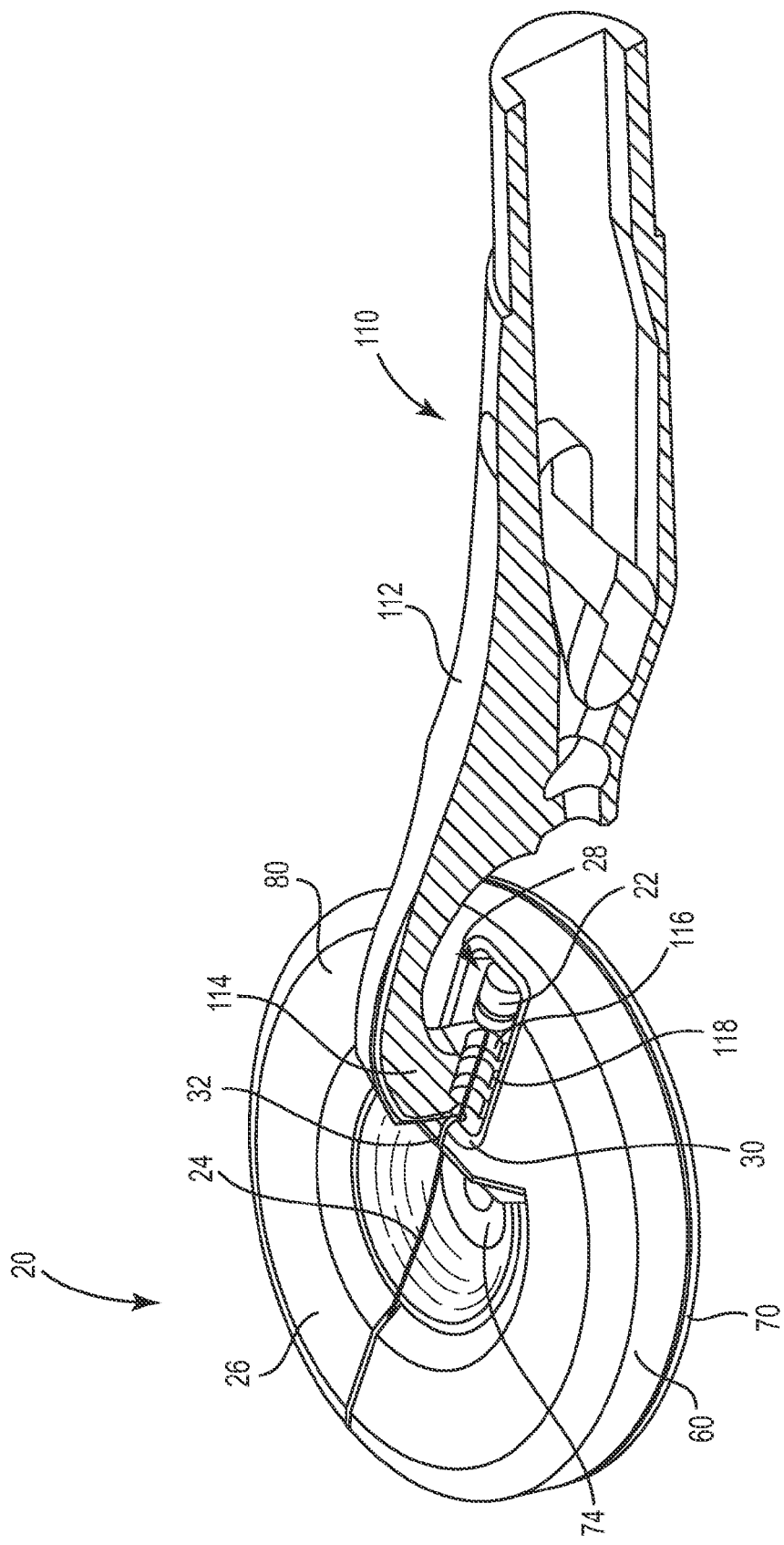
FIG. 7 is a perspective view of the suture assembly illustrated in FIG. 1 loading suture onto a suture instrument according to one embodiment.

FIG. 7 is a perspective view of one embodiment of a suture system 110 including a suture instrument 112 being loaded with suture 24 from suture assembly 20.

In one embodiment, suture instrument 112 includes ahead 114 having a distal end that is insertable into capsule retainer 28. In one suitable example, capsule retainer 28 is provided as a radial recess formed in exterior surface 80 of first flange 60, where the recess is aligned with a center of the first flange 60, although other arrangements for capsule retainer 28 are also acceptable. The distal end of instrument 112 defines a cavity 116 sized to capture capsule 22, and in one embodiment is provided with a slot 118 that slides over suture 24 to enable head 114 to be retracted rearward to capture capsule 22 in cavity 116. Wall 32 aligns capsule 22 and suture 24 to enable head 114 to enter retainer 28 and engage capsule 22. Suture 24 may be controllably removed from suture container 26 after instrument 112 is so engaged with capsule 22.

Figure 8:
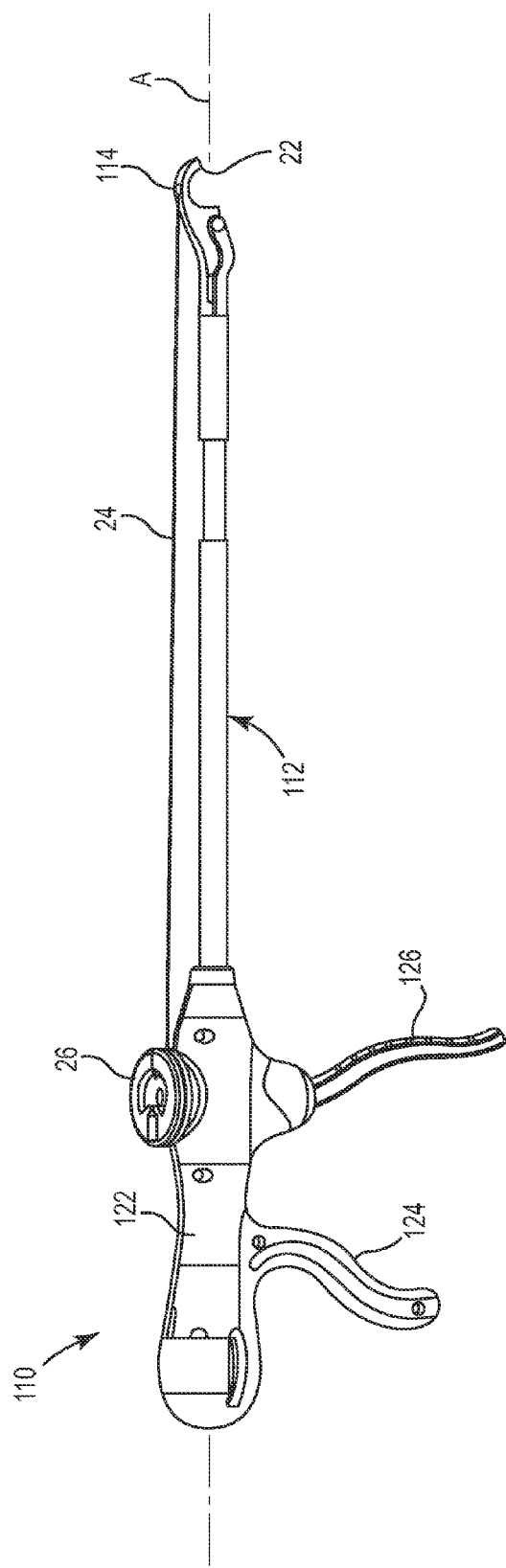
FIG. 8 is a perspective view of a suture system including the suture assembly illustrated in FIG. 1 attached to a handle of a suture instrument according to one embodiment.

FIG. 8 is a perspective side view of one embodiment of suture system 110 including suture instrument 112 cooperating with container 26 to load suture 24 onto instrument 112. Suture instrument 112 is oriented along a major axis A and includes a handle on 122 providing a palm rest 124 and a trigger 126. Capsule 22 has been captured within cavity 116 of distal end of head 114 (FIG. 7), and suture container 26 is attached to handle 122 such that suture 24 is held in tension between the head 114 and the handle 122 of instrument 112. In one embodiment, suture container 26 is attached to a top portion of handle 122 and suture 24 is aligned within a groove formed in a top curved portion of distal end of head 114. In this configuration, container 26 and handle 122 combine to align suture 24 parallel with the major axis A of suture instrument 112, which offers the surgeon a one-piece system for intracorporeal suture delivery that minimizes suture tangling.

Figure 9:
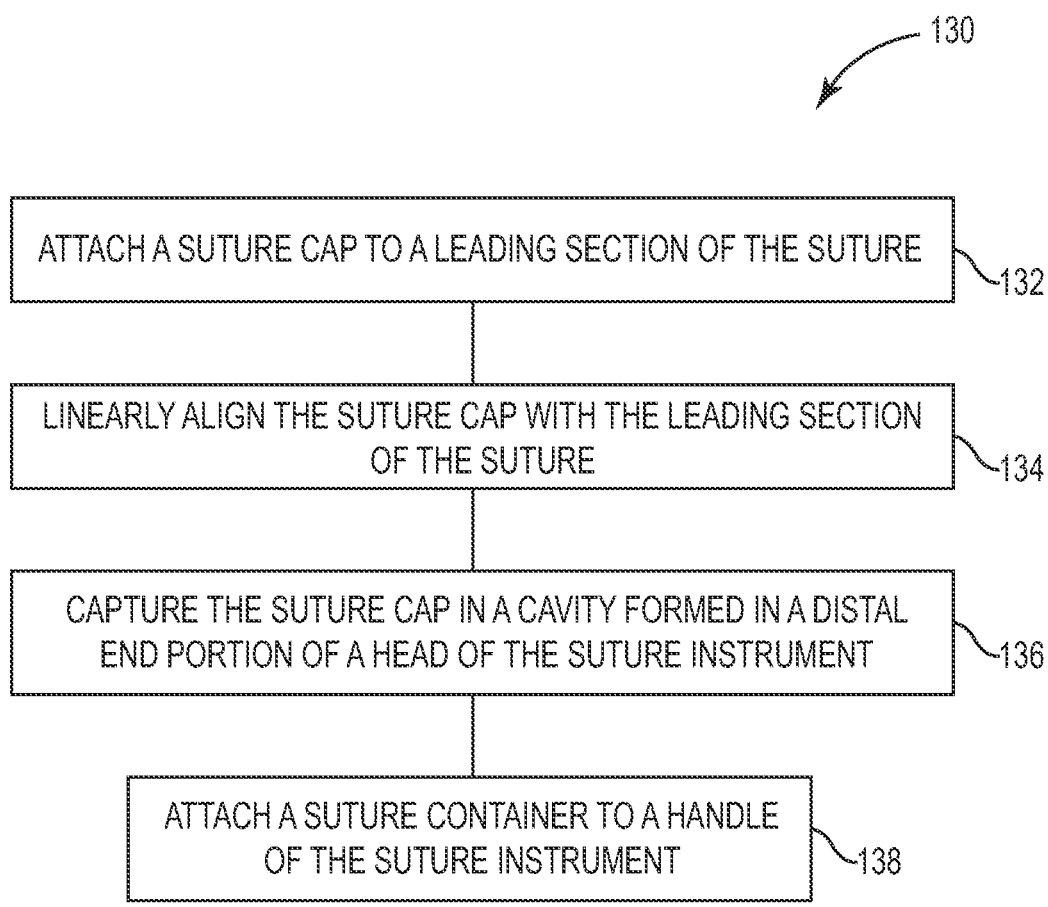
FIG. 9 is a flow diagram of a method of manufacturing and loading a suture instrument with suture according to one embodiment.

FIG. 9 is a flow diagram 130 of a method of manufacturing and loading suture into a suture instrument. Flow diagram 130 includes attaching a suture capsule a leading section of suture at 132, and linearly aligning the suture capsule with the leading section of the suture at 134. Flow diagram 130 provides capturing the suture capsule in a cavity of a distal end portion of a head of the suture instrument at 136. At 138, a suture container is attached to a handle of the suture instrument to tension the suture between a head and the handle of the suture instrument.

Exemplary embodiments of employing the suture assembly 20 described above in accordance with a flow diagram 130 are provided below in the surgical treatment of pelvic organ prolapse.

The patient is prepared for the surgical procedure by having a catheter placed in the patient's urethra, along with other recommended, desirable, or preliminary steps in preparation for the surgery. For example, the patient is typically placed on an operating table in a lithotomy position with the buttocks extending just beyond an edge of the table. With the patient under anesthesia, a vaginal incision (female) or a perineal incision (male) is made by the surgeon. Thereafter, the surgeon would typically palpate the patient (e.g., digitally) to identify a desired landmark, such as the sacrospinous ligament or arcus tendineous ligament. The surgeon subsequently introduces sterile suture instrument 112 (e.g., by guiding instrument along an extended index finger in contact with the identified landmark) and engages the distal end of head 114 (FIG. 8) with the identified landmark.

A needle is driven from a proximal portion of the suturing head 114 through the tissue of the identified landmark. For example, the surgeon activates trigger 126 to drive a needle out of a proximal end portion of head 114, through the tissue of the identified landmark, and into engagement with the recess 46 (FIG. 2) of capsule 22.

The needle forms a lesion in the tissue, and upon retraction of the needle, capsule 22 is pulled back through the lesion with suture 24 following behind. In this manner, a stitch is placed in the identified landmark with one end of suture 24 attached to capsule 22 and an opposite end of suture 24 attached to needle 54. Pelvic organ support mesh is threaded onto needle 54. A pulley knot is formed by crossing the capsule end of suture 24 over the needle end of suture. The support mesh is directed along suture 24 with the pulley knot and into contact with the identified landmark (e.g., a ligament). The surgeon terminates the support mesh to the ligament according to his/her established preference, for example by tying one or more knots in suture 24, and snips off capsule 22 and needle 54. This approach is repeated, and after placement of a suitable number of sutures into the landmark to retain the support mesh, as determined by the surgeon, the head 114 is disengaged from the landmark and suturing instrument 112 is removed from the patient. The pelvic organ support mesh is selected by the surgeon and could be synthetic material or tissue material (human tissue or animal tissue suitably prepared as a support).

Suture container 26 provides cap retainer 28 integrally formed in the exterior surface 80 of flange 60. Other embodiments of suture containers are described below.

Figure 10:
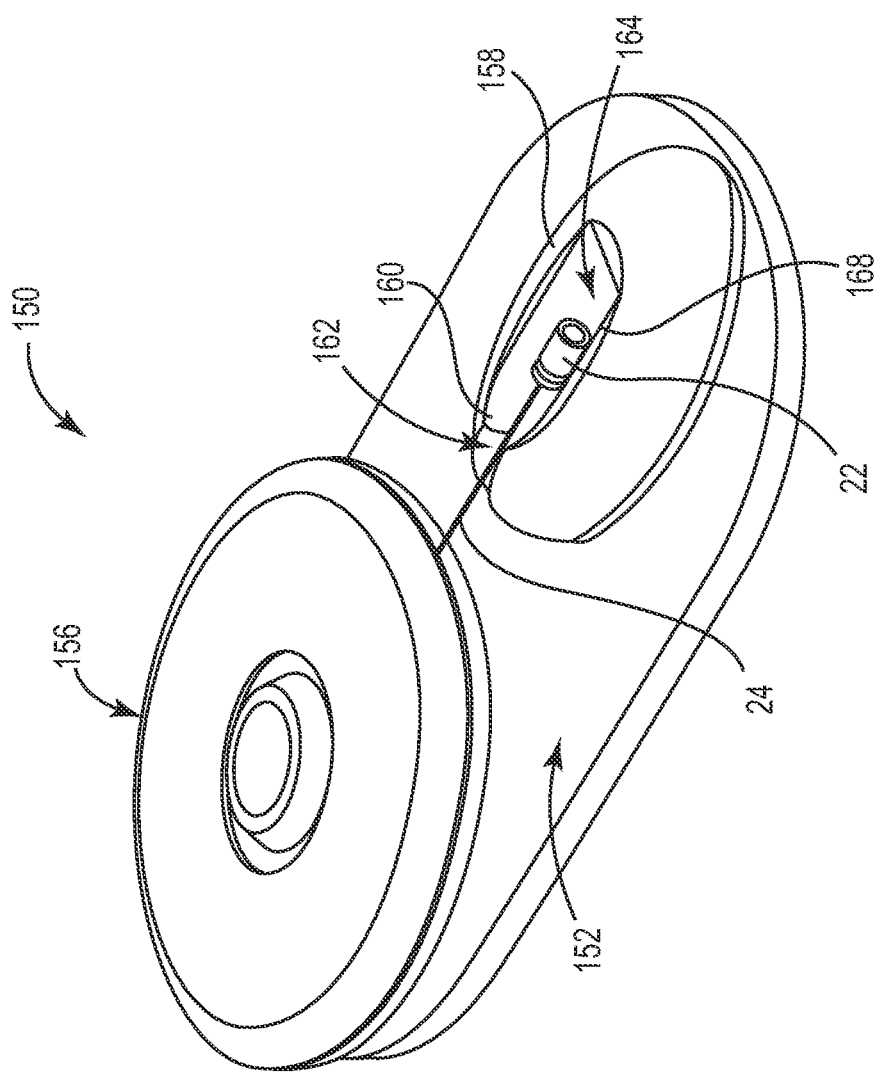
FIG. 10 is a perspective view of another embodiment of a suture assembly.

FIG. 10 is a perspective view of one embodiment of a suture assembly 150. Suture assembly 150 includes a base substrate 152, a suture container 156 removably attached to a base substrate 152, and a capsule retainer 158 integrally formed with base substrate 152. In one embodiment, suture container 156 is provided as a spool with suture 24 wound onto the spool and capsule 22 stowed and retained within capsule retainer 158. Substrate 152 and suture container 156 are preferably fabricated from plastic suited for sterilization by conventional means, such as ethylene oxide or gamma ray sterilization.

In one embodiment, capsule retainer 158 is integrally formed on one end of base substrate 152 and includes a wall 160 and a suture channel 162 formed in wall 160 to communicate with a capsule reservoir 164. A length of suture 24 is inserted into suture channel 162 to align suture 24 with capsule 22. Capsule 22 is stored in capsule reservoir 164 and held in position by wall 160 and suture channel 162. In one embodiment, capsule reservoir 164 is provided as an opening defined by a continuous peripheral wall 168 that extends integrally from substrate 152. In one embodiment, a length of capsule reservoir 164 is greater than a width of capsule reservoir 160 for such that capsule 22 is aligned within reservoir 164 for extraction by suture instrument 110 (FIG. 8).

Figure 11:
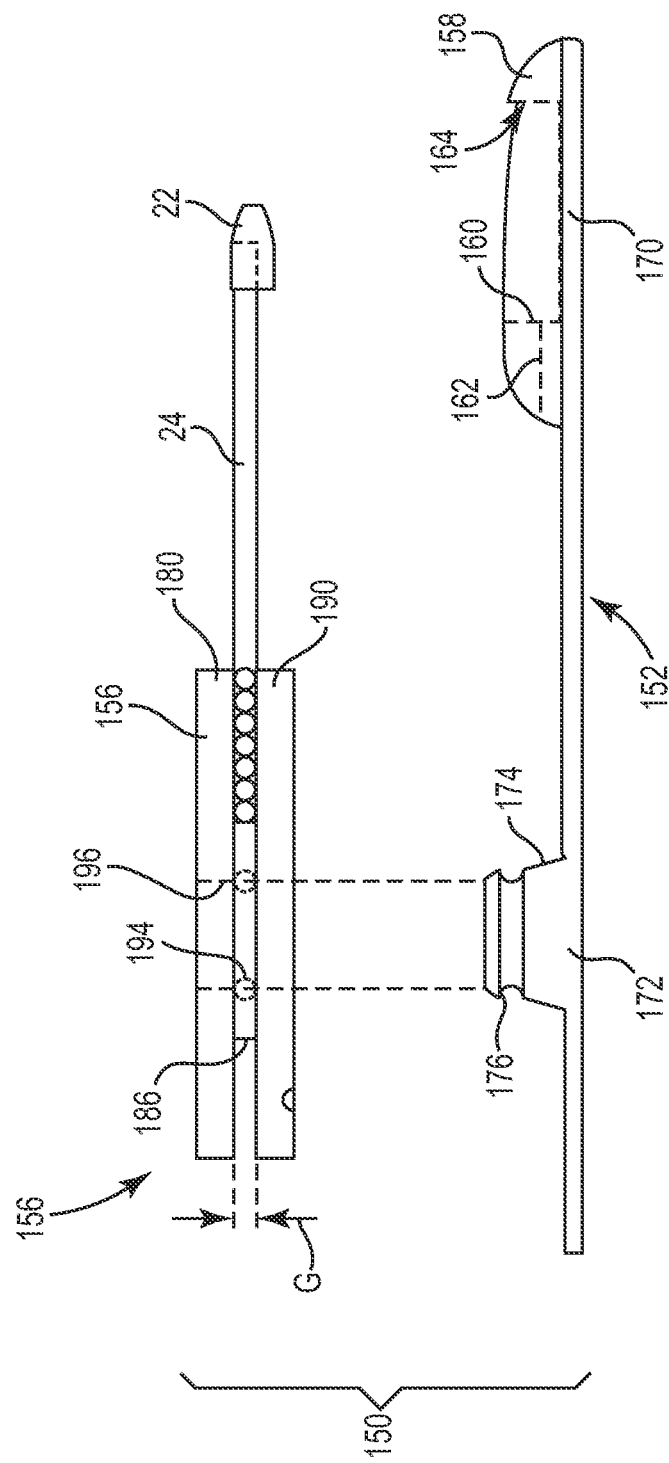
FIG. 11 is an exploded side view of the suture assembly illustrated in FIG. 10 according to one embodiment.

FIG. 11 is an exploded side view of suture assembly 150. In one embodiment, base substrate 152 includes a proximal end portion 170 opposite a distal end portion 172, where capsule retainer 158 is integrally formed on proximal end portion 170 and the suture container 156 is removably attached to a post 174 formed on distal end portion 172. In one embodiment, suture channel 162 is formed in wall 160 at a location that is nearest to post 174.

In one embodiment, post 174 is integrally formed to extend from base substrate 152 and includes a retention notch 176 sized to frictionally engage with suture container 156. In one embodiment, suture container 156 is provided as a reel that includes a first flange 180 attached to a second flange 190, where the flanges 180, 190 are spaced apart by a suture gap G to provide a suture winding surface 186. In one embodiment, suture gap G is approximately equal to or less than the diameter of suture 24, such that when suture 24 is wound onto suture winding surface 186, each successive winding of suture 24 is spaced apart from suture winding surface 186 by the diameter of suture 24. As a consequence of this structure, suture 24 may be unwound from suture container 156 in a substantially tangle-free manner.

In one embodiment, suture container 156 is similar to suture container 26 (FIG. 3) described above and includes an O-ring 194 exposed in a central hole 196. The central hole 196 is sized to fit over post 174 such that O-ring 194 engages with notch 176. In this manner, suture container 156 is configured to be pressed-fit onto post 174 for delivery to the operating room, and snapped apart from substrate 152 for use in the operating room and ultimately for attachment to the handle of suture instrument 112.

Figure 12:
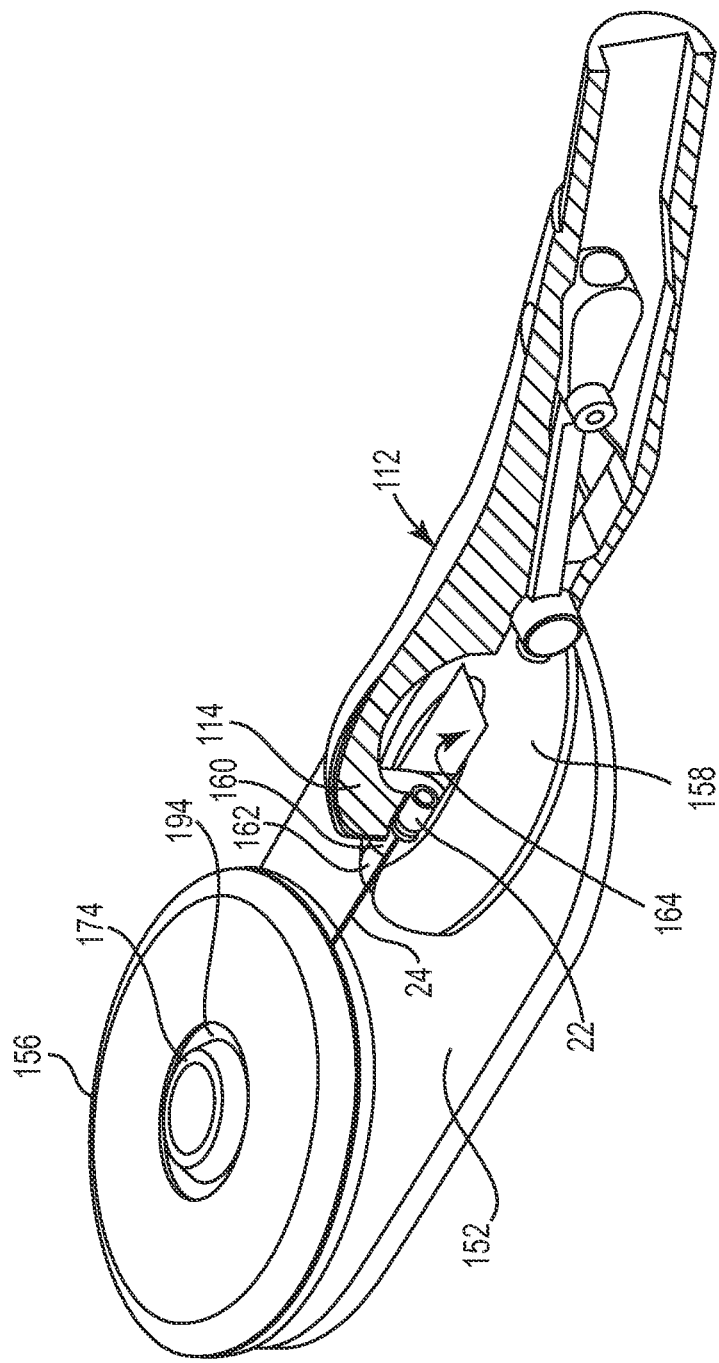
FIG. 12 is a perspective view of the suture assembly illustrated in FIG. 10 loading suture onto a suture instrument.
Figure 13:
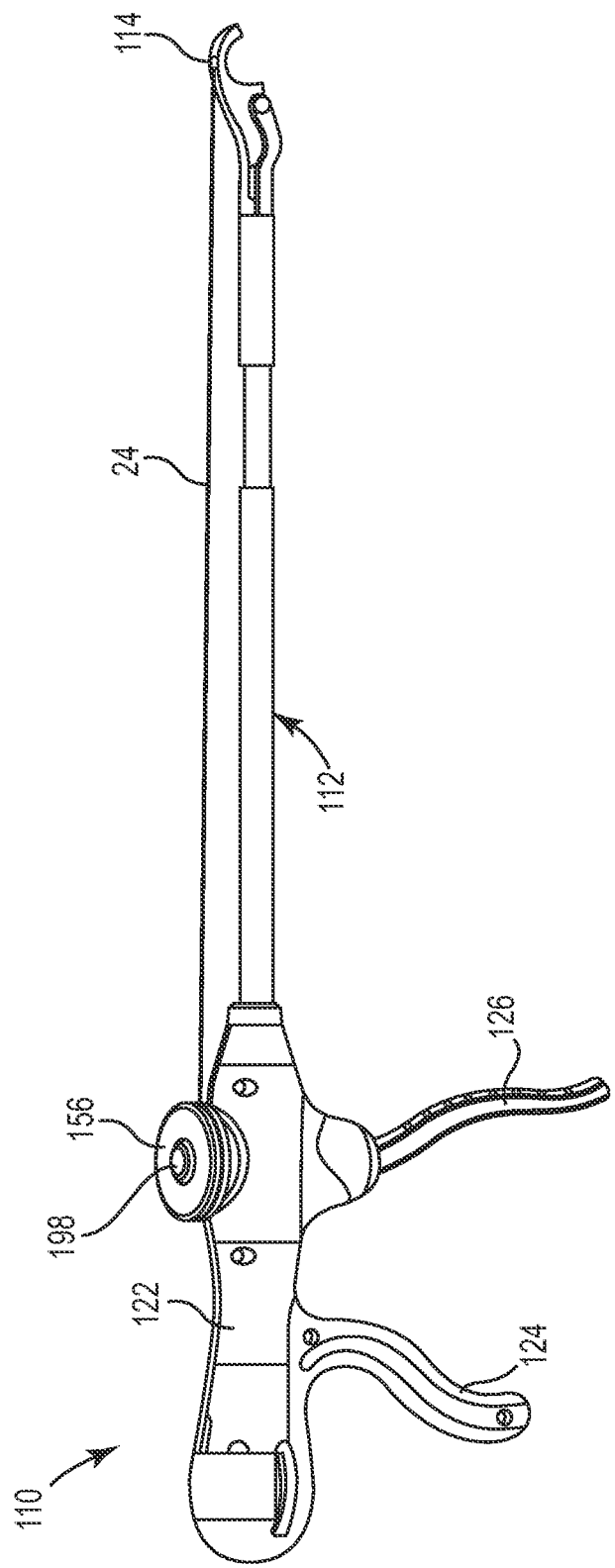
FIG. 13 is a perspective view of a suture system including the suture assembly illustrated in FIG. 10 attached to a handle of a suture instrument.

FIG. 12 is a perspective view of suture container 156 loading suture 24 onto instrument 112 and FIG. 13 is a perspective view of suture instrument 112 loaded with suture and suture container 156 attached to suture instrument 112.

FIG. 12 is a perspective view of capsule 22 and suture 24 aligned for engagement with head 114 of instrument 112. Wall 160 and channel 162 combine to align suture 24 and retain capsule 22 within capsule reservoir 164 to enable the distal end of head 114 to enter capsule reservoir 164 and engage capsule 22. As head 114 extracts capsule 22, suture 24 is unwound from suture container 156. Suture container 156 is removable from substrate 152 to selectively tension suture 24 onto instrument 112.

FIG. 13 is a perspective view of suture system 110 including suture container 156 attached to suture instrument 112. Capsule 22 is retained within distal end of head 114, and suture 24 is tensioned between end 114 and handle 122. In one embodiment, handle 122 is provided with a post 198 that is similar to post 174 (FIG. 11), and suture container 156 is snapped onto post 198 to maintain suture 24 in tension.

Figure 14:
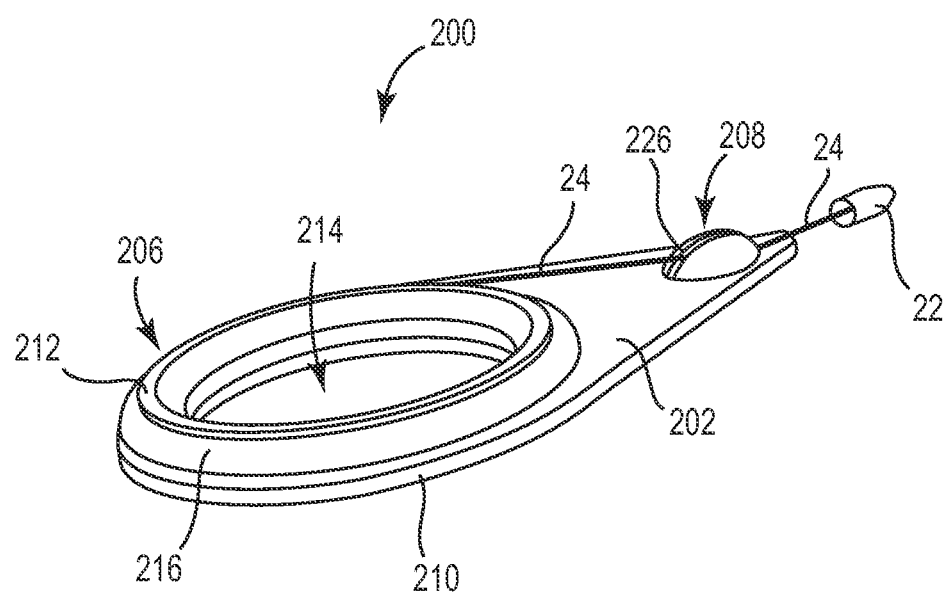
FIG. 14 is a perspective view of another embodiment of a suture assembly.

FIG. 14 is a perspective view and FIG. 15 is a side cross-sectional view of one embodiment of a suture assembly 200. The suture assembly 200 includes a base substrate 202, a suture retainer 206, and a capsule retainer 208 integrally formed with the base substrate 202.

Suture retainer 206 is provided on a proximal end portion 210 of substrate 202 and includes a fence 212 surrounding a hole 214, where fence 212 is integrally formed with base substrate 202. In one embodiment, fence 212 is circular and hole 214 is a ring sized to receive a finger/thumb of a user. The user holds suture assembly 200 such that proximal end portion 210 is nearest the user. Suture 24 is configured to be wound around fence 212. In one embodiment, an O-ring 216 is fitted onto fence 212 and is configured to engage and retain suture between fence 212 and O-ring 216.

In one embodiment, capsule retainer 208 is provided on a distal end portion 220 of the substrate 202 and includes a riser 222 that defines a proximal end 224 of base substrate 202. In one embodiment, riser 222 as provided as a hemi-spherical bead of material and includes a suture channel 226 formed in the bead. Riser 222 thus provides a wall formed by end 224 of base substrate 202, where the wall is configured to deny passage of capsule 22 through suture channel 226 and align capsule 22 with suture 24 for loading into the suture instrument 112 (FIG. 8).

In one embodiment, substrate 202, riser 222, and fence 212 are integrally formed as a monolithic unit fabricated from disposable material such as plastic. In one embodiment, hole 214 is sized to receive a thumb such that suture assembly 200 may be slid over a thumb of the surgeon to manage the alignment and delivery of suture 24. For example, during use the capsule retainer 208 aligns capsule 22 and a portion of suture 24 for engagement by suture instrument 112 (FIG. 8). The remaining portion of suture assembly 200 is controlled by the surgeon who slides his or her thumb through hole 214 to control the removal of suture 24 from suture retainer 206.

Suture assemblies are described that are configured to load suture instruments with suture. The suture assemblies each include a suture container configured to retain a portion of the suture, and a cap retainer configured to retain a cap (or capsule) that is attached to one end of the suture. The cap retainer includes a wall and a suture channel formed in the wall, where the wall is configured to deny passage of the cap into the suture channel and thus align the capsule with a length of suture for loading the suture into the surgical instrument. The suture systems and assemblies described herein enable the rapid and convenient loading of a suture instrument with suture with improved control of suture deployment.

Although specific embodiments have been illustrated and described herein, it will be appreciated by those of ordinary skill in the art that a variety of alternate and/or equivalent implementations may be substituted thr the specific embodiments shown and described without departing from the scope of the present invention. This application is intended to cover any adaptations or variations of medical devices as discussed herein. Therefore, it is intended that this invention be limited only by the claims and the equivalents thereof.

EMBODIMENTS

1. A suture assembly configured to load a suture instrument with suture, the suture assembly comprising:
    a cap attached to an end of the suture;
    a suture container configured to retain a portion of the suture; and
    a cap retainer comprising a wall and a suture channel formed in the wall, the suture channel configured to receive a length of the suture, and the wall configured to deny passage of the cap into the suture channel and align the cap with the length of the suture for loading into the suture instrument.

2. The suture assembly of embodiment 1, wherein the suture container comprises:
    a first flange extending from a first reel segment; and
    a second flange extending from a second reel segment, the first and second reel segments attached to provide a suture winding surface and the first flange spaced apart from the second flange by a suture gap.

3. The suture assembly of embodiment 2, wherein the suture defines a suture diameter and the suture gap is less than the suture diameter.

4. The suture assembly of embodiment 2, wherein the cap retainer is integrally formed as a recess in an exterior surface of the first flange.

5. The suture assembly of embodiment 4, wherein the recess is a radial recess having a major axis aligned with a center of the first flange.

6. The suture assembly of embodiment 2, wherein a portion of the first tee segment mates with a portion of the second reel segment to provide a suture winding surface.

7. The suture assembly of embodiment 6, further comprising:
    an O-ring disposed between the first reel segment and the second reel segment.

8. The suture assembly of embodiment 7, wherein each of the first and second reel segments define a center hole such that the center hole in the first reel segment aligns with the center hole in the second reel segment, the O-ring exposed within the center holes.

9. The suture assembly of embodiment 2, comprising a needle attached to an end of the suture opposite the cap, and an exterior surface of the second flange defines a needle groove sized to frictionally retain the needle.

10. The suture assembly of embodiment 1, wherein the wall separates the cap from the portion of the suture retained by the suture container.

11. The suture assembly of embodiment 1 further comprising:
    a base substrate;
    wherein the cap retainer is formed on a first end portion of the base substrate and the suture container is attached to a second end portion of the base substrate opposite of the first end portion.

12. The suture assembly of embodiment 11, wherein the cap retainer comprises a riser integrally formed on a surface of the base substrate, the wall comprising an end of the riser, and the suture container comprises a circular fence integrally formed on the surface of the base substrate around which the suture is wound.

13. The suture assembly of embodiment 12, further comprising:
    an opening formed through the base substrate and the suture container, the opening surrounded by the circular fence to define a ring sized to receive a finger/thumb of a user of the suture instrument.

14. The suture assembly of embodiment 11, wherein the cap retainer comprises a cap reservoir defining an opening sized to contain the cap, and the suture container comprises a reel removably attached to the base substrate and attachable to the suture instrument.

15. The suture assembly of embodiment 14, wherein the cap reservoir comprises a continuous peripheral wall extending from a surface of the base substrate to surround and define the opening, and the suture channel is formed in the continuous peripheral wall to communicate with the opening at a location nearest to the movable reel.

16. The suture assembly of embodiment 14, wherein a length of the opening of the cap reservoir is greater than a width of the opening of the cap reservoir and so configured to align the cap for extraction from the cap retainer by a head of the suture instrument.

17. The suture assembly of embodiment 14, wherein the reel comprises a first flange extending from a first reel segment and a second flange extending from a second reel segment, the first and second reel segments attached to provide a suture winding surface and the first flange spaced apart from the second flange by a suture gap.

18. The suture assembly of embodiment 17, wherein each of the first and second reel segments defines a central hole sized to be press-fit onto a post formed on a handle of the suture instrument.

19. The suture assembly of embodiment 1, wherein the wall and the suture channel combine to orient the cap linearly with the length of the suture.

20. A suture assembly configured to load a suture instrument with suture, the suture assembly comprising:
a cap attached to one end of the suture, the cap comprising a leading end separated from a trailing end by a body, the leading end of the cap configured to move through tissue ahead of the trailing end of the cap and defining a recess sized to receive a needle of the suture instrument;
a suture container configured to retain a trailing section of the suture; and
means for tensioning the suture between the cap and the trailing section of the suture.

21. The suture assembly of embodiment 20, comprising a base substrate, the suture container coupled to the base substrate.

22. The suture assembly of embodiment 21 wherein the suture container comprises a stationary suture container integrally formed with the base substrate.

23. The suture assembly of embodiment 22, comprising a cap retainer integrally formed with the base substrate and spaced apart from the suture container, the cap retainer comprising a hemispherical riser defining a suture channel sized to receive a leading section of the suture and retain the cap in a location spaced apart from the suture container.

24. The suture assembly of embodiment 21, wherein the suture container comprises a reel onto which the trailing section of the suture is wound, the reel removable from the base substrate and attachable to the suture instrument.

25. The suture assembly of embodiment 24, comprising a cap retainer comprising a continuous peripheral wall attached to the base substrate, the wall surrounding a recess sized to receive the cap and defining a suture channel sized to receive a leading section of the suture such that the cap is retained in the opening and spaced apart from the suture container.

26. The suture assembly of embodiment 20, herein the suture container comprises:
a first flange extending from a first reel segment; and
a second flange extending from a second reel segment, the first and second reel segments attached to provide a suture winding surface and the first flange spaced apart from the second flange by a suture gap;
wherein the first flange defines a recess that is sized to receive the cap and separate the cap from the trailing section of the suture.

27. The suture assembly of embodiment 20, wherein a diameter of the leading end of the cap is smaller than a diameter of the trailing end of the cap.

28. The suture assembly of embodiment 20, wherein the recess formed in the leading end of the cap is sized to receive a needle of the suture instrument.

29. The suture assembly of embodiment 20, herein the one end of the suture is molded to the body of the cap.

30. A suture system comprising:
a suture instrument comprising a handle located proximal and a head located distal relative the suture instrument, the head comprising a distal end that defines a cavity; and
a suture assembly comprising a cap attached to an end of suture, a suture container maintaining a trailing section of the suture and attachable to the handle, and a cap retainer isolating the cap from the trailing section of the suture;
wherein, when the cap is captured in the cavity of the distal end of the head and the suture container is attached to the handle, the suture is tensioned between the head and the handle of the suture instrument.

31. The suture system of embodiment 30, wherein the suture assembly comprises a card, the suture container comprising a reel removably attached to the card, and the cap retainer comprising a recess formed in the card and sized to receive the distal end of the head of the suture instrument.

32. The suture system of embodiment 31, wherein the recess formed in the card is formed by a continuous wall extending from the card to surround and define the recess.

33. The suture system of embodiment 32, wherein the wall defines a suture channel configured to receive a leading end section of the suture, and the cap disposed in the recess is isolated from the suture container by the wall.

34. The suture system of embodiment 30, wherein the suture container comprises:
a first flange extending from a first reel segment; and
a second flange extending from a second reel segment, the first and second reel segments attached to provide a suture winding surface and the first flange spaced apart from the second flange by a suture gap that enables removal of the suture from the suture winding surface;
wherein the cap retainer is a recess that is integrally formed in the first flange.

35. The suture system of embodiment 34, wherein the recess is integrally formed in an exterior surface of the first flange such that the cap disposed in the recess is isolated from the trailing section of the suture by the first flange.

36. The suture system of embodiment 34, wherein the handle comprises a post, and each of the first flange and the second flange defines a central hole that is sized to be snap-fit onto the post of the handle.

37. The suture system of embodiment 30, wherein the cap comprises a substantially cylindrical body.

38. The suture system of embodiment 37, wherein the cavity in the distal end of the head is formed as a substantially cylindrical cavity sized to receive the substantially cylindrical body of the cap.

39. The suture system of embodiment 38, wherein the suture instrument comprises a needle and a leading end of the cap defines a recess sized to receive the needle.

40. The suture system of embodiment 39, wherein the needle is deployed from a proximal end portion of the head of the suture instrument and is configured to pull the leading end of the cap through tissue ahead of a trailing end of the cap.

41. A method of loading suture into a suture instrument, the method comprising:
attaching a suture cap to a leading section of the suture;
linearly aligning the suture cap with the leading section of the suture;
capturing the suture cap in a cavity formed in a distal end portion of a head of the suture instrument; and
attaching a suture container to a handle of the suture instrument.

42. The method of embodiment 41, wherein the handle comprises a proximal end opposite a distal end, and attaching the suture container to the handle of the suture instrument between the proximal end and the distal end.

43. The method of embodiment 42, comprising attaching the suture container to a top surface of the handle of the suture instrument between the proximal end and the distal end.

44. The method of embodiment 41, comprising capturing a substantially cylindrical suture cap in a substantially cylindrical cavity formed in the distal end portion of the suture instrument.

45. The method of embodiment 41, wherein the suture container comprises a reel removably attached to a base substrate, the base substrate defining a cap reservoir, and linearly aligning the suture cap with the leading section of the suture comprises disposing the suture cap in the cap reservoir and engaging the leading section of the suture in a suture channel formed in a wall of the cap reservoir.

46. The method of embodiment 45, comprising:
 extracting the suture cap from the cap reservoir with the distal end portion of the suture instrument; and
 removing the reel from the base substrate.

47. The method of embodiment 41, wherein the suture container comprises a first flange separated from a second flange by a suture winding surface, an exterior surface of the first flange defining a cap reservoir configured to retain the cap, the method comprising:
 extracting the cap from the cap reservoir with the distal end portion of the suture instrument.

48. A suture assembly configured to load a suture instrument with suture including a capsule attached to an end of the suture, the suture assembly comprising:
 a suture container configured to retain a portion of the suture, the suture container comprising a first flange communicating with a second flange via a suture winding surface onto which the suture is wound, at least one of the first and second flanges defining a recess configured to retain the capsule.

49. The suture assembly of embodiment 48, wherein the suture comprises a suturing needle attached to an end of the suture opposite of the capsule, an exterior surface of the first flange defining the recess configured to retain the capsule and an exterior surface of the second flange defining a needle groove configured to retain the suturing needle.

50. The suture assembly of embodiment 49, wherein the recess formed in the first flange comprises a wail and a suture channel formed in the wall, the suture channel configured to receive a length of the suture, and the wall configured to deny passage of the capsule into the suture channel and align the cap with the length of the suture for loading into the suture instrument.

51. The suture assembly of embodiment 48, wherein the first flange is spaced apart from the second flange by a suture gap, the suture gap sized to be approximately equal to a diameter of the suture.

52. The suture assembly of embodiment 48, wherein the first flange is spaced apart from the second flange by a suture gap, the suture gap less than a diameter of the suture.

53. The suture assembly of embodiment 48, wherein the first flange, the second flange, and the suture winding surface are formed as a single monolithic unit.

What is claimed is:

1. A suture system comprising:
 a suture instrument comprising a handle located proximal and a head located distal relative the suture instrument, the head comprising a movable needle that moves within the head from a proximal portion of the head to a distal end of the head that defines a cavity; and
 a suture assembly comprising a cap attached to an end of suture, a suture container maintaining a trailing section of the suture and attachable to the handle, and a cap retainer isolating the cap from the trailing section of the suture;
 wherein the cap is a tubular cap having a body wall formed around an open tubular through-bore, the tubular cap insertable into the cavity of the head such that the open tubular through-bore is aligned to removably receive a tissue-piercing pointed end of the movable needle of the head of the instrument;
 wherein, when the tubular cap is captured in the cavity of the distal end of the head and the suture container is attached to the handle, the suture is tensioned between the head and the handle of the suture instrument; and
 wherein the suture container comprises:
 a first flange extending from a first reel segment; and
 a second flange extending from a second reel segment, the first and second reel segments coupled to one another to provide a suture winding surface, the first flange spaced apart from the second flange by a suture gap equal to or less than a diameter of the suture to allow the suture to be friction-fit within the suture gap, the first and the second flanges further capturing an O-ring between them such that a portion of the O-ring is exposed within a central hole defined in the first and the second flanges.

2. The suture system of claim 1, wherein the suture assembly comprises a card and the suture container is removably attached to the card.

3. The suture system of claim 1, wherein a recess is integrally formed in an exterior surface of the first flange such that the tubular cap disposed in the recess is isolated from the trailing section of the suture by the first flange.

4. The suture system of claim 1, wherein the handle comprises a post, and the central hole is sized to be snap-fit onto the post.

5. The suture system of claim 1, wherein the tubular cap comprises a substantially cylindrical body.

6. The suture system of claim 5, wherein the cavity in the distal end of the head is formed as a substantially cylindrical cavity sized to receive the substantially cylindrical body of the tubular cap.

7. The suture system of claim 1, wherein the needle is deployed from a proximal end portion of the head of the suture instrument and is configured to engage with the tubular through-bore of the tubular cap and pull a leading end of the tubular cap through tissue ahead of a trailing end of the tubular cap.

8. A method of loading suture into a suture instrument, the method comprising:
 providing a tubular suture cap that is attached to a leading section of the suture, the tubular suture cap having a body wall formed around a tubular through-bore;
 capturing the tubular suture cap in a cavity formed in a distal end portion of a head of the suture instrument such that the suture extends out of a distal end of the head of the suture instrument;
 attaching a suture container that retains a portion of the suture to a handle of the suture instrument;
 wherein the suture container comprises a first flange separated from a second flange by a suture gap equal to or less than a diameter of the suture to form a suture winding surface from which suture winding surface suture is removable;
 moving a needle within the head of the suture instrument from a proximal portion of the head into the tubular through-bore of the tubular suture cap and removing the tubular suture cap with the needle from the cavity formed in the distal end portion of the head; and removing the needle of the suture instrument from the tubular through-bore of the tubular suture cap.

9. The method of claim 8, comprising capturing a substantially cylindrical tubular suture cap in a substantially cylindrical cavity formed in the distal end portion of the suture instrument.

10. The method of claim 8, wherein an exterior surface of the first flange defines a cap reservoir that is sized to allow the tubular suture cap to be placed into the cap reservoir.

11. The method of claim 8, wherein the suture container is attached to an exterior portion of the handle.

\* \* \* \* \*

UNITED STATES PATENT AND TRADEMARK OFFICE
CERTIFICATE OF CORRECTION

| | |
|---|---|
| PATENT NO. | : 8,920,440 B2 |
| APPLICATION NO. | : 12/850644 |
| DATED | : December 30, 2014 |
| INVENTOR(S) | : Steven McClurg et al. |

It is certified that error appears in the above-identified patent and that said Letters Patent is hereby corrected as shown below:

Title page, item [73] assignee should read as follows: Coloplast A/S, Humlebaek (DK)

Signed and Sealed this
Fourteenth Day of April, 2015

Michelle K. Lee
*Director of the United States Patent and Trademark Office*